(12) United States Patent
Lee et al.

(10) Patent No.: US 9,307,955 B2
(45) Date of Patent: Apr. 12, 2016

(54) ULTRASOUND DIAGNOSTIC METHOD AND ULTRASOUND DIAGNOSTIC APPARATUS USING VOLUME DATA

(71) Applicant: SAMSUNG MEDISON CO., LTD., Gangwon-do (KR)

(72) Inventors: Jin-yong Lee, Gangwon-do (KR); Sung-wook Park, Gangwon-do (KR); Eun-jung Chang, Gangwon-do (KR)

(73) Assignee: SAMSUNG MEDISON CO., LTD., Hongcheon-Gun, Gangwon-Do (KR)

( * ) Notice: Subject to any disclaimer, the term of this patent is extended or adjusted under 35 U.S.C. 154(b) by 192 days.

(21) Appl. No.: 13/919,832

(22) Filed: Jun. 17, 2013

(65) Prior Publication Data

US 2014/0163380 A1     Jun. 12, 2014

(30) Foreign Application Priority Data

Dec. 7, 2012     (KR) ........................ 10-2012-0142308

(51) Int. Cl.
*A61B 8/00*     (2006.01)
*A61B 8/08*     (2006.01)
*A61B 8/06*     (2006.01)
*A61B 8/14*     (2006.01)
(Continued)

(52) U.S. Cl.
CPC . *A61B 8/488* (2013.01); *A61B 8/06* (2013.01); *A61B 8/4488* (2013.01); *A61B 8/483* (2013.01); *A61B 8/08* (2013.01); *A61B 8/14* (2013.01); *A61B 8/4444* (2013.01); *A61B 8/469* (2013.01); *A61B 8/523* (2013.01); *A61B 8/543* (2013.01); *G01S 7/52074* (2013.01); *G01S 15/8979* (2013.01); *G01S 15/8993* (2013.01)

(58) Field of Classification Search
CPC ........ A61B 8/5238; A61B 8/13; A61B 8/483; A61B 8/0883; A61B 8/06; G01S 15/8993
USPC .................................................. 600/437–469
See application file for complete search history.

(56) References Cited

U.S. PATENT DOCUMENTS 5,365,929 A  *  11/1994  Peterson .................. A61B 8/06
                                                                       128/916
5,993,390 A     11/1999  Savord et al.
6,241,675 B1 *  6/2001  Smith ...................... A61B 8/06
                                                                       128/916
(Continued)

FOREIGN PATENT DOCUMENTS

EP       1 798 573 A2     6/2007
JP       2000-166926 A    6/2000
(Continued)

OTHER PUBLICATIONS

Korean Office Action issued in corresponding Korean Application No. 10-2012-0142308, dated Jul. 31, 2014, with English translation.
(Continued)

*Primary Examiner* — Sanjay Cattungal
(74) *Attorney, Agent, or Firm* — McDermott Will & Emery LLP

(57) ABSTRACT

A method and apparatus for measuring a Doppler signal by using volume data. In detail, the method and apparatus measure a Doppler signal by obtaining a sub volume by using a color component of volume data and locating a sample volume on a scan line of a cell whose corresponding sub volume is scanned.

17 Claims, 9 Drawing Sheets

(51) Int. Cl.
  *G01S 15/89* (2006.01)
  *G01S 7/52* (2006.01)

(56) References Cited

U.S. PATENT DOCUMENTS

| | | | | |
|---|---|---|---|---|
| 6,544,175 B1* | 4/2003 | Newman | ............... | A61B 8/00 |
| | | | | 600/437 |
| 6,589,179 B2 | 7/2003 | Criton et al. | | |
| 6,692,441 B1* | 2/2004 | Poland | ............... | G06T 15/08 |
| | | | | 128/916 |
| 7,425,198 B2* | 9/2008 | Moehring | ............... | A61B 8/06 |
| | | | | 600/454 |
| 2004/0073111 A1* | 4/2004 | Poland | ............... | G06T 7/0028 |
| | | | | 600/437 |
| 2004/0092816 A1* | 5/2004 | Ossmann | ............... | A61B 5/0456 |
| | | | | 600/428 |
| 2004/0215077 A1* | 10/2004 | Witt | ............... | A61B 8/06 |
| | | | | 600/443 |
| 2005/0228280 A1* | 10/2005 | Ustuner | ............... | A61B 8/06 |
| | | | | 600/443 |
| 2007/0038103 A1* | 2/2007 | Kobayashi | ............... | A61B 8/14 |
| | | | | 600/443 |
| 2007/0078344 A1* | 4/2007 | Rafter | ............... | A61B 8/08 |
| | | | | 600/450 |
| 2008/0208053 A1 | 8/2008 | Hashimoto | | |
| 2008/0242996 A1 | 10/2008 | Hall et al. | | |
| 2009/0030313 A1* | 1/2009 | Prater | ............... | A61B 8/14 |
| | | | | 600/443 |
| 2009/0149757 A1* | 6/2009 | Liu | ............... | A61B 8/0883 |
| | | | | 600/447 |
| 2009/0192386 A1* | 7/2009 | Hashimoto | ............... | A61B 8/00 |
| | | | | 600/443 |
| 2009/0203996 A1* | 8/2009 | Thiele | ............... | A61B 8/467 |
| | | | | 600/441 |
| 2010/0228127 A1* | 9/2010 | Allain | ............... | A61B 8/08 |
| | | | | 600/443 |

FOREIGN PATENT DOCUMENTS

| | | |
|---|---|---|
| JP | 2009-172223 A | 8/2009 |
| KR | 10-2008-0047042 A | 5/2008 |
| WO | 01/71376 A1 | 9/2001 |

OTHER PUBLICATIONS

Extended European Search Report issued in European Patent Application No. EP 13166733.9 dated Jul. 31, 2013.
Final Office Action issued in Korean Application No. 10-2012-00142308, dated Jan. 26, 2015, with English translation.
Reexamination issued in Korean Application No. 10-2012-00142308, dated Mar. 31, 2015, with English translation.

* cited by examiner

ULTRASOUND DIAGNOSTIC METHOD AND ULTRASOUND DIAGNOSTIC APPARATUS USING VOLUME DATA

CROSS-REFERENCE TO RELATED PATENT APPLICATION

This application claims the benefit of Korean Patent Application No. 10-2012-0142308, filed on Dec. 7, 2012, in the Korean Intellectual Property Office, the disclosure of which is incorporated herein in its entirety by reference.

BACKGROUND OF THE INVENTION

1. Field of the Invention

The present invention relates to an ultrasound diagnostic method and apparatus for diagnosing a target by using volume data, and more particularly, to a method and apparatus for measuring a Doppler signal and diagnosing a target by accurately setting a location of a sample volume in volume data.

2. Description of the Related Art

An ultrasound diagnostic apparatus generates an ultrasound signal (generally equal to or higher than 20 kHz) by using a probe, and obtains an image of a predetermined region inside a target by using information about a reflected echo signal. Specifically, the ultrasound diagnostic apparatus is used for medical purposes, for example, detecting a foreign body in the target, measuring an injury in the target, and observing inside the target. Such an ultrasound diagnostic apparatus is widely used along with other image diagnostic apparatuses, since the ultrasound diagnostic apparatus has high stability compared to using x-rays, can display an image in real-time, and is safe in terms of radiation exposure.

An image (hereinafter, referred to as an ultrasound image) obtained from the ultrasound diagnostic apparatus may be displayed on the ultrasound diagnostic apparatus or may be stored in a storage medium and displayed on an image display apparatus. For example, the ultrasound image may be reduced and displayed on a screen of a mobile phone, a portable electronic device, a personal digital assistant (PDA), or a tablet personal computer (PC).

Meanwhile, in a Doppler mode wherein a moving speed, a moving direction, and pressure of a target at a predetermined location are measured, reliability of result data differs according to a Doppler angle, which is an angle formed by an ultrasound signal emitted from a transducer and the moving direction of the target. In other words, when a Doppler angle is 20° or higher, a measured Doppler signal and received information about movement of a target are not accurate.

SUMMARY OF THE INVENTION

When a location of a sample volume for measuring a Doppler signal is determined on a 2-dimensional (2D) sliced image, it is difficult to accurately set a location and angle of the sample volume. Accordingly, the present invention provides an ultrasound diagnostic method and apparatus for efficiently obtaining a Doppler signal with high reliability by using volume data. The present invention also provides a computer-readable recording medium having recorded thereon a program for executing the ultrasound diagnostic method.

According to an aspect of the present invention, an ultrasound diagnostic method includes obtaining a sub volume whose Doppler signal is to be measured based on a color component of at least one sliced image by cutting a 3-dimensional (3D) image according to 3-dimensional (3D) volume data of a target in a predetermined direction. A cell corresponding to the sub volume is determined from among a plurality of cells included in a transducer. The at least one sliced image is displayed, and a scan line is displayed on each of the at least one sliced image, wherein the scan line is irradiated by the determined cell. Additionally, direction information of the scan line is displayed on the at least one sliced image, and a sample volume for obtaining a Doppler signal is located on the scan line.

According to another aspect of the present invention, an ultrasound diagnostic apparatus includes a transducer, an image processor, a sub volume extractor, a cell determiner, a display unit, and a Doppler processor. The transducer is configured to scan a target. The image processor is configured to generate 3-dimensional (3D) volume data of the target, and to obtain at least one sliced image by cutting a 3D image according to the 3D volume data in a predetermined direction. The sub volume extractor is configured to obtain a sub volume whose Doppler signal is to be measured, based on a color component of the at least one sliced image. The cell determiner is configured to determine a cell corresponding to the sub volume from among a plurality of cells included in the transducer. The display unit is configured to display the at least one sliced image, display a scan line on each of the at least one sliced image wherein the scan line is irradiated by the determined cell, and display direction information of the scan line on the at least one sliced image. Finally, the Doppler processor is configured to locate a sample volume for obtaining a Doppler signal, on the scan line.

According to a further aspect of the present invention, a computer-readable recording medium is provided having recorded thereon a program for executing the ultrasound diagnostic method.

BRIEF DESCRIPTION OF THE DRAWINGS

The above and other features and advantages of the present invention will become more apparent by describing in detail exemplary embodiments thereof with reference to the attached drawings in which.

DETAILED DESCRIPTION OF THE INVENTION

All terms including descriptive or technical terms which are used herein should be construed as having meanings that are obvious to one of ordinary skill in the art. However, the terms may have different meanings according to an intention of one of ordinary skill in the art, precedent cases, or the appearance of new technologies. Also, some terms may be arbitrarily selected by the applicant, and in this case, the meaning of the selected terms will be described in detail in the detailed description of the invention. Thus, the terms used herein have to be defined based on the meaning of the terms together with the description throughout the specification.

Also, when a part "includes" or "comprises" an element, unless there is a particular description contrary thereto, the part can further include other elements, not excluding the other elements. In the following description, terms such as "unit" and "module" indicate a unit for processing at least one function or operation, wherein the unit and the block may be embodied as hardware or software or embodied by combining hardware and software.

Herein, a "target" may be a subject of an ultrasound diagnosis. However, the "target" is not limited to the whole body of the subject, but may be a part of the subject, i.e., a predetermined region, a tissue, or blood of the subject. In other words, the "target" may be a predetermined region that reflects an emitted ultrasound signal. Also, the subject is not limited to a body.

Hereinafter, one or more embodiments of the present invention will be described in detail with reference to accompanying drawings.

Figure 1:
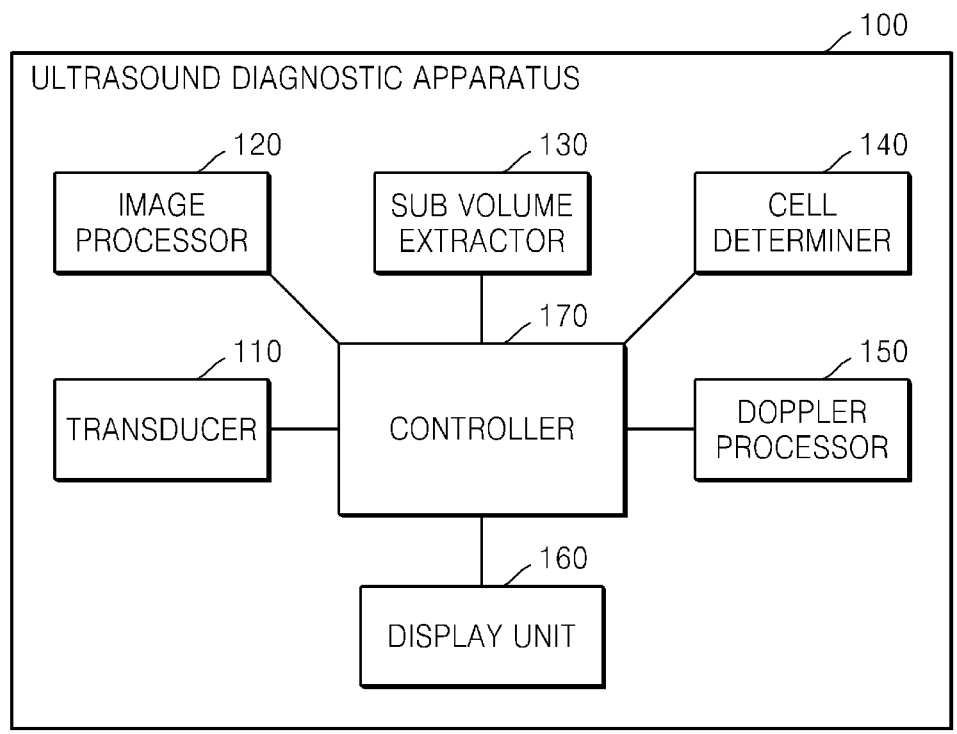
FIG. 1 is a block diagram of an ultrasound diagnostic apparatus according to an embodiment of the present invention.

FIG. 1 is a block diagram of an ultrasound diagnostic apparatus 100 according to an embodiment of the present invention. The ultrasound diagnostic apparatus 100 may include a transducer 110, an image processor 120, a sub volume extractor 130, a cell determiner 140, a Doppler processor 150, a display unit 160, and a controller 170. The embodiment shown in FIG. 1 is only an example, and the ultrasound diagnostic apparatus 100 may further include other general-purpose components.

The ultrasound diagnostic apparatus 100 generates an ultrasound image by scanning a target. In other words, the ultrasound diagnostic apparatus 100 generates the ultrasound image by emitting an ultrasound signal to the target through the transducer 110 and receiving an echo signal reflected from the target. The ultrasound diagnostic apparatus 100 may further include 3-dimensional (3D) volume data as well as a 2D image indicating a sliced image of the target.

Also, the ultrasound diagnostic apparatus 100 may not only generate a gray scale ultrasound image obtained by scanning the target in an A mode (amplitude mode), a B mode (brightness mode), and an M mode (motion mode), but also generate a Doppler image indicating a motion of the target in colors by using color information included in Doppler data. The Doppler image generated by the ultrasound diagnostic apparatus 100 may include at least one of a blood flow Doppler image (or a color Doppler image) showing a blood flow, and a tissue Doppler image indicating a motion of tissues.

Meanwhile, the ultrasound diagnostic apparatus 100 may not only directly obtain an ultrasound image by using the transducer 110, but may also receive an ultrasound image and Doppler data from an external device through a communicator (not shown) via a wired or wireless network. For example, the ultrasound diagnostic apparatus 100 may receive various types of data, such as an ultrasound image and Doppler data related to the ultrasound image, from a cloud server or another device in a hospital server, through a picture archiving and communication system (PACS).

The transducer 110 emits the ultrasound signal to the target and receives the echo signal reflected from the target. In other words, the transducer 110 may include a plurality of cells or elements for emitting and receiving an ultrasound signal, and may be included in a probe (not shown) along with a unit for deriving the transducer 110. Meanwhile, the transducer 110 may obtain Doppler data indicating a motion of the target.

Meanwhile, the transducer 110 may irradiate a scan line by performing a steering process on one or more cells or elements. In other words, the transducer 110 may form a beam heading towards the target, i.e., the scan line, by focusing an ultrasound signal emitted from at least one cell. Accordingly, the ultrasound diagnostic apparatus 100 is able to match a cell or element to a scan line included in a 2D or 3D ultrasound image. In other words, the ultrasound diagnostic apparatus 100 may determine a corresponding relation between a predetermined scan line and a cell of the transducer 110.

According to an embodiment, the probe including the transducer 110 may include a matrix probe wherein a plurality of cells are arranged according to 2D coordinates. In other words, the transducer 110 may emit and receive an ultrasound signal for generating 3D volume data by using the plurality of cells.

According to another embodiment, the transducer 110 may scan the target according to cardiac cycles of the target. Accordingly, the ultrasound diagnostic apparatus 100 may generate the 3D volume data by combining one or more pieces of volume data obtained according to the cardiac cycles.

The image processor 120 generates an ultrasound image and several pieces of graphic information based on the echo signal received from the target. For example, the image processor 120 may generate a 2D ultrasound image or a 3D ultrasound image based on the 3D volume data. Also, the image processor 120 may generate a sliced image by dividing the 3D volume data. In addition, the image processor 120 may generate a Doppler image based on Doppler data obtained through the transducer 110.

Furthermore, the image processor 120 may also generate a scan line according to at least one cell included in the transducer 110. In other words, the image processor 120 may generate a scan line connecting a predetermined location on an ultrasound image and a cell of the transducer 110. The image processor 120 will be described in detail later with reference to FIG. 2.

The sub volume extractor 130 determines and extracts a sub volume included in an ultrasound image generated by the image processor 120. The sub volume may denote a 3D ultrasound image having a predetermined size, which is generated from 3D volume data. Alternatively, the sub volume may denote a partial region of a 2D ultrasound image.

Meanwhile, the sub volume extractor 130 may extract the sub volume based on a color component of volume data. In other words, when the image processor 120 generates a Doppler image expressed in colors based on Doppler data, a color component of the Doppler image may denote motion of the target, i.e., motion of blood or tissues.

In other words, the sub volume extractor 130 may extract the sub volume at a location indicating the motion of blood or tissues, based on the color component included in the Doppler image. Alternatively, the sub volume extractor 130 may obtain the sub volume based on a color component of volume data or sliced image, or based on a user input received from a user. Details about obtaining a sub volume will be described in detail later with reference to FIGS. 5 and 8.

The cell determiner 140 selects one or more cells from among the plurality of cells or elements included in the transducer 110. In other words, the cell determiner 140 may select and determine at least one cell corresponding to the sub volume extracted by the sub volume extractor 130, from among the plurality of cells. In other words, since the transducer 110 irradiates the scan line generated by steering the plurality of cells, the cell determiner 140 may determine at least one cell whose corresponding sub volume having a predetermined size is scanned from among the cells included in the transducer 110. Details will be described later with reference to FIG. 6.

The Doppler processor 150 measures a Doppler signal indicating a moving speed or pressure of the target at a predetermined location. In other words, the Doppler processor 150 may locate a sample volume for receiving a Doppler signal at a desired depth of the target through a pulsed wave (PW) mode. Furthermore, the Doppler processor 150 may measure a Doppler signal indicating a location of the sample volume.

According to an embodiment, the Doppler processor 150 may locate the sample volume on a scan line. In other words, the Doppler processor 150 may locate the sample volume at one point on the scan line selected by an external input signal. Details will be described later with reference to FIG. 7.

The display unit 160 displays several ultrasound images and information generated by the image processor 120. For example, the display unit 160 may display not only a 2D or 3D ultrasound image, but also various types of data, such as a sub volume, a sample volume, a Doppler image, and a scan line, on a screen.

According to an embodiment, the display unit 160 may display a sub volume included in 3D volume data, and also display a scan line for scanning a determined sub volume. Meanwhile, when the display unit 160 displays one or more sliced images, a scan line may be displayed with respect to each sliced image. Details will be described later with reference to FIG. 9.

Meanwhile, the display unit 160 may include at least one of a liquid crystal display (LCD), a thin film transistor (TFT) LCD, an organic light-emitting diode (OLED), a flexible display, and a 3D display. Alternatively, the ultrasound diagnostic apparatus 100 may include at least two display units 160 according to its shape.

According to an embodiment, the display unit 160 may include a user input unit (not shown) for receiving an external input, and a touch screen having a layer structure. In other words, the display unit 160 may be used both as an output device and an input device, and at this time, the display unit 160 may receive a touch input via a stylus pen or a part of a body such as a finger.

Also, as described above, when the display unit 160 is a touch screen and has a layer structure, the display unit 160 may detect a location, area, and pressure of a touch input. Also, the touch screen may not only detect a real-touch but also a proximity touch.

The controller 170 controls several components included in the ultrasound diagnostic apparatus 100 in general. In other words, the controller 170 may control the image processor 120 to process data obtained by the transducer 110 and generate an ultrasound image. Alternatively, the controller 170 may control the cell determiner 140 to select a cell corresponding to a sub volume selected by the sub volume extractor 130, or control the display unit 160 to display a scan line of the selected sub volume.

Figure 2:
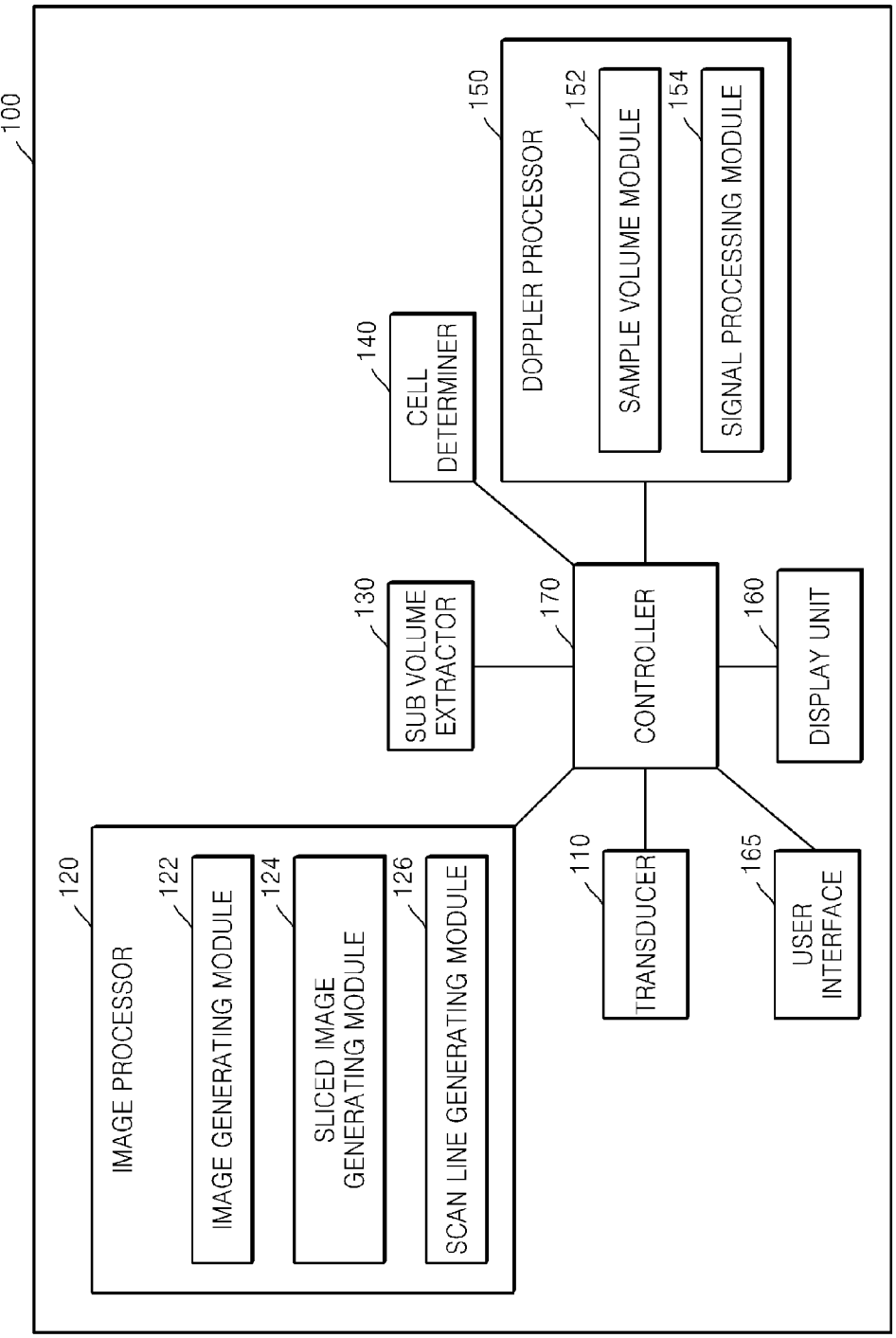
FIG. 2 is a block diagram of the ultrasound diagnostic apparatus according to another embodiment of the present invention.

FIG. 2 is a block diagram of the ultrasound diagnostic apparatus 100 according to another embodiment of the present invention. Descriptions of components of FIG. 2 that overlap those of FIG. 1 will not be repeated.

The image processor 120 may include an image generating module 122, a sliced image generating module 124, and a scan line generating module 126. Each module included in the image processor 120 will now be described in detail.

The image generating module 122 generates a 2D or 3D ultrasound image based on volume data. Also, the image generating module 122 may not only generate a gray scale ultrasound image, but also a Doppler image expressed in colors. In other words, the image generating module 122 may generate a Doppler image by using a color map where motion of a target and a color are matched.

The sliced image generating module 124 generates at least one sliced image obtained by cutting a 3D ultrasound image. In other words, the sliced image generating module 124 may generate a 2D ultrasound image obtained by cutting volume data in a predetermined direction.

Meanwhile, the sliced image may include at least one of an A plane image according to an axial view of the target, a B plane image according to a sagittal view of the target, and a C plane image according to a coronal view of the target. Alternatively, the sliced image generating module 124 may receive a user input for selecting a location of volume data to be cut to obtain a sliced image through a user interface 165, and obtain the sliced image based on the user input.

The scan line generating module 126 generates a scan line irradiated by at least one cell corresponding to a sub volume of the target. The generating of the scan line by the scan line generating module 126 may mean that a scan line to be displayed by the display unit 160 is expressed by using graphic data, unlike an ultrasound signal emitted by the transducer 110. When a plurality of ultrasound images are displayed on a screen, the scan line generating module 126 may generate a scan line to be displayed on each sliced image.

The Doppler processor 150 may include a sample volume module 152 and a signal processing module 154. The sample volume module 152 locates a sample volume at a depth for obtaining a Doppler signal. Meanwhile, the sample volume module 152 may determine a location of the sample volume based on an external input signal received through the user interface 165. In other words, when a user input for selecting any one location on a scan line is received, the sample volume module 152 may locate the sample volume at the corresponding location.

The signal processing module 154 measures a Doppler signal of the sample volume. In other words, the signal processing module 154 may receive information about a moving speed, a moving direction, and a pressure of a target at the location where the sample volume is located, and analyze the information.

The user interface 165 provides various information about photographing and diagnosing of the target to a user, and receives a user input for controlling the ultrasound diagnostic apparatus 100 from the user. In other words, the user interface 165 may display information about an ultrasound image and a scan line on a screen, or display a sliced image of the volume data on the screen. Meanwhile, the user interface 165 may be realized inside the display unit 160. In other words, the user interface 165 for outputting an ultrasound image and various information may be included in the display unit 160.

The user interface 165 may receive a user input via any one of various input units, such as a mouse, a keyboard, a keypad, a touch pad, a touch screen, and a trackball. In other words, the user interface 165 may receive a user input for controlling an operation of the ultrasound diagnostic apparatus 100, for example, may receive a user input for selecting any one location on a scan line or for selecting a location for cutting volume data.

In addition to the description of FIG. 1, the controller 170 may also control the user interface 165. In other words, the controller 170 may locate the sample volume based on the user input received through the user interface 165, or control various components to obtain a sliced image.

Hereinafter, ultrasound diagnostic methods for diagnosing a target through volume data by using the components included in the ultrasound diagnostic apparatus 100 will be described with reference to FIGS. 3 and 4.

Figure 3:
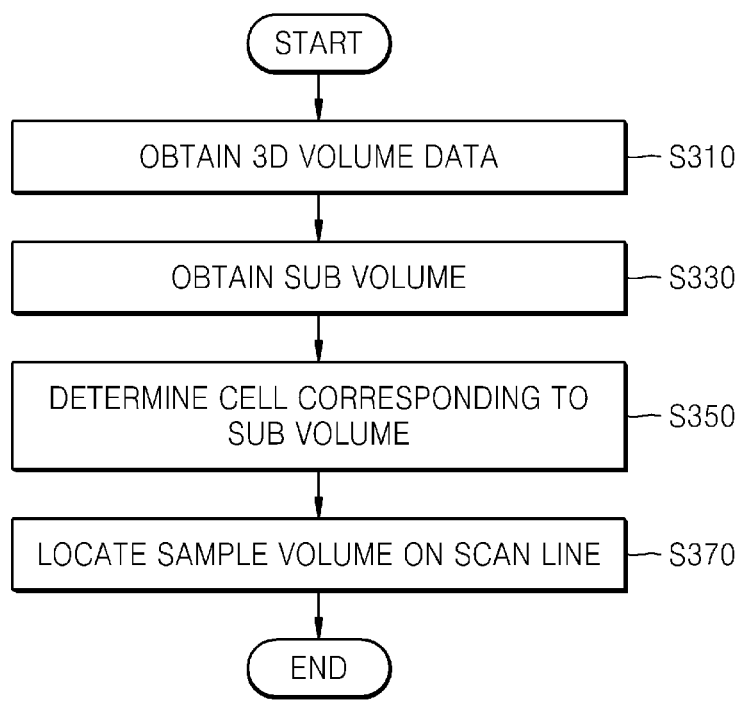
FIG. 3 is a flowchart illustrating an ultrasound diagnostic method according to an embodiment of the present invention.
Figure 4:
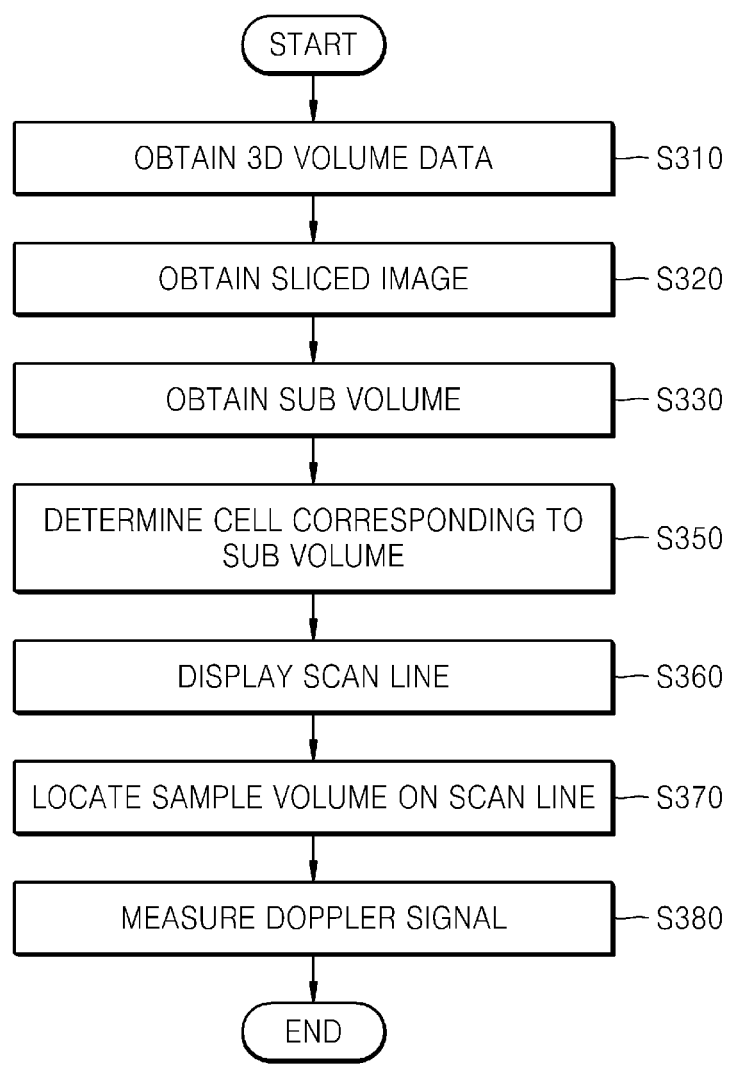
FIG. 4 is a flowchart illustrating an ultrasound diagnostic method according to another embodiment of the present invention.

The ultrasound diagnostic methods of FIGS. 3 and 4 include operations sequentially performed by the ultrasound diagnostic apparatus 100, the transducer 110, the image processor 120, the sub volume extractor 130, the cell determiner 140, the Doppler processor 150, the display unit 160, the user interface 165, and the controller 170 of FIGS. 1 and 2. Accordingly, details described with reference to FIGS. 1 and 2 are also applied to those of FIGS. 3 and 4.

FIG. 3 is a flowchart illustrating an ultrasound diagnostic method according to an embodiment of the present invention.

In operation S310, the ultrasound diagnostic apparatus 100 obtains 3D volume data. In other words, the ultrasound diagnostic apparatus 100 obtains volume data by scanning a target. Meanwhile, the ultrasound diagnostic apparatus 100 may obtain volume data all at the same time by using a matrix probe, or obtain 3D volume data by combining data dividedly obtained according to cardiac cycles of the target as described above.

Meanwhile, the volume data obtained by the ultrasound diagnostic apparatus 100 in operation S310 may include a color component based on Doppler data. In other words, the volume data may express a blood flow or a motion of tissues in colors, and the ultrasound diagnostic apparatus 100 may obtain and display the volume data including the color component.

In operation S330, the ultrasound diagnostic apparatus 100 obtains a sub volume included in the 3D volume data. In other words, the ultrasound diagnostic apparatus 100 may extract a sub volume for measuring a Doppler signal from the volume data based on the color component of the volume data.

In detail, since the color component of the volume data expresses a blood flow or a motion of tissues, the ultrasound diagnostic apparatus 100 may determine the sub volume where a sample volume for measuring a Doppler signal is to be located, by using the color component. Meanwhile, the ultrasound diagnostic apparatus 100 may determine the sub volume by using color information of a sliced image, as will be described in detail later with reference to FIG. 4.

According to an embodiment, the ultrasound diagnostic apparatus 100 may determine the sub volume based on a user input. In other words, the ultrasound diagnostic apparatus 100 may display a 3D ultrasound image including a color component on a screen, and determine a sub volume based on a user input for selecting any one location on the 3D ultrasound image.

In operation S350, the ultrasound diagnostic apparatus 100 determines a cell corresponding to the sub volume. In other words, the ultrasound diagnostic apparatus 100 may determine one or more cells whose corresponding sub volume obtained in operation S330 is scanned, from among a plurality of cells included in the transducer 110. Since the target is scanned by a beam focused via a steering process performed on the plurality of cells included in the transducer 110, the ultrasound diagnostic apparatus 100 may obtain information about a cell whose location with respect to a sub volume included in volume data is scanned from the transducer 110 and the controller 170.

In operation S370, the ultrasound diagnostic apparatus 100 locates a sample volume on a scan line. In other words, the ultrasound diagnostic apparatus 100 may locate the sample volume on the scan line irradiated by the one or more cells determined in operation S350. In other words, the ultrasound diagnostic apparatus 100 may accurately locate the sample volume for measuring a Doppler signal on the scan line via the cell whose corresponding sub volume obtained in operation S330 is scanned.

Meanwhile, in operation S370, the ultrasound diagnostic apparatus 100 may locate the sample volume based on a user input for selecting any one location on the scan line. After operation S370, the ultrasound diagnostic apparatus 100 may measure the Doppler signal of the sample volume.

FIG. 4 is a flowchart illustrating an ultrasound diagnostic method according to another embodiment of the present invention. Details of FIG. 4 that have been described above with reference to FIG. 3 will not be repeated.

In operation S320, the ultrasound diagnostic apparatus 100 obtains a sliced image from 3D volume data. In other words, the ultrasound diagnostic apparatus 100 may obtain one or more sliced images by cutting a 3D ultrasound image.

In operation S320, the ultrasound diagnostic apparatus 100 may obtain a sliced image based on a color component of volume data. In other words, the ultrasound diagnostic apparatus 100 may obtain at least one sliced image by cutting a region or space including a color component in volume data. For example, the ultrasound diagnostic apparatus 100 may obtain at least one sliced image from among an A cross section, a B cross section, and a C cross section regarding regions including color components in a 3D ultrasound image.

Meanwhile, the ultrasound diagnostic apparatus 100 may obtain at least one sliced image based on a user input. In other words, when a user input for selecting a location of a sliced image is received from a user, the ultrasound diagnostic apparatus 100 may obtain one or more sliced images based on the user input.

In operation S330, the ultrasound diagnostic apparatus 100 obtains a sub volume by using a color component of the at least one sliced image. In other words, the ultrasound diagnostic apparatus 100 may determine a sub volume for locating a sample volume for measuring a motion of the target, based on a color component expressed in each sliced image.

Alternatively, in operation S330, the ultrasound diagnostic apparatus 100 may obtain the sub volume based on a user input for selecting a location of the sub volume. In other words, the ultrasound diagnostic apparatus 100 may receive a user input for selecting any one location on a sliced image from a user, and obtain a sub volume based on the user input.

In operation S350, the ultrasound diagnostic apparatus 100 determines one or more cells corresponding to the sub volume determined in operation S330. In other words, the ultrasound diagnostic apparatus 100 may determine one or more cells whose corresponding sub volume is scanned, from among the plurality of cells included in the transducer 110.

In operation S360, the ultrasound diagnostic apparatus 100 displays a scan line irradiated by the determined cell. In other words, the ultrasound diagnostic apparatus 100 may display a scan line irradiated by the one or more cells determined in operation S350 on an ultrasound image. For example, the ultrasound diagnostic apparatus 100 may display the scan line on the volume data or on each of the at least one sliced image.

In operation S370, the ultrasound diagnostic apparatus 100 locates a sample volume on the scan line. As described with reference to FIG. 3, the ultrasound diagnostic apparatus 100 may locate the sample volume based on a user input for selecting any one location on the scan line.

In operation S380, the ultrasound diagnostic apparatus 100 measures a Doppler signal. In other words, the ultrasound diagnostic apparatus 100 may measure a Doppler signal indicating a motion of the target at a location of the sample volume located in operation S370.

Figure 5:
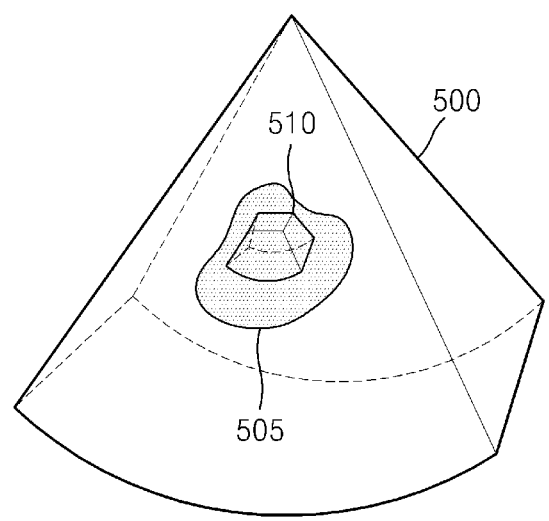
FIG. 5 is a diagram for describing obtaining of a sub volume from volume data, according to an embodiment of the present invention.

FIG. 5 is a diagram for describing obtaining of a sub volume from a 3D ultrasound image 500, according to an embodiment of the present invention. The 3D ultrasound image 500 of FIG. 5 may include a color region 505 where a motion of a target is expressed in colors. In other words, the color region 505 is a region including a color component for expressing a blood flow or a motion of tissues shown in the 3D ultrasound image 500.

Meanwhile, according to the embodiment shown in FIG. 5, the ultrasound diagnostic apparatus 100 obtains a sub volume 510 by using the color component of the 3D ultrasound image 500. In other words, the ultrasound diagnostic apparatus 100 may obtain the sub volume 510 as a candidate region for locating a sample volume. Meanwhile, the ultrasound diagnostic apparatus 100 may obtain the sub volume 510 included in the color region 505 of the 3D ultrasound image 500 by using the color component of the 3D ultrasound image 500.

Meanwhile, the ultrasound diagnostic apparatus 100 may obtain the sub volume 510 by using one or more sliced images obtained by cutting the 3D ultrasound image 500 in a predetermined direction, as will be described in detail later with reference to FIG. 8.

Figure 6:
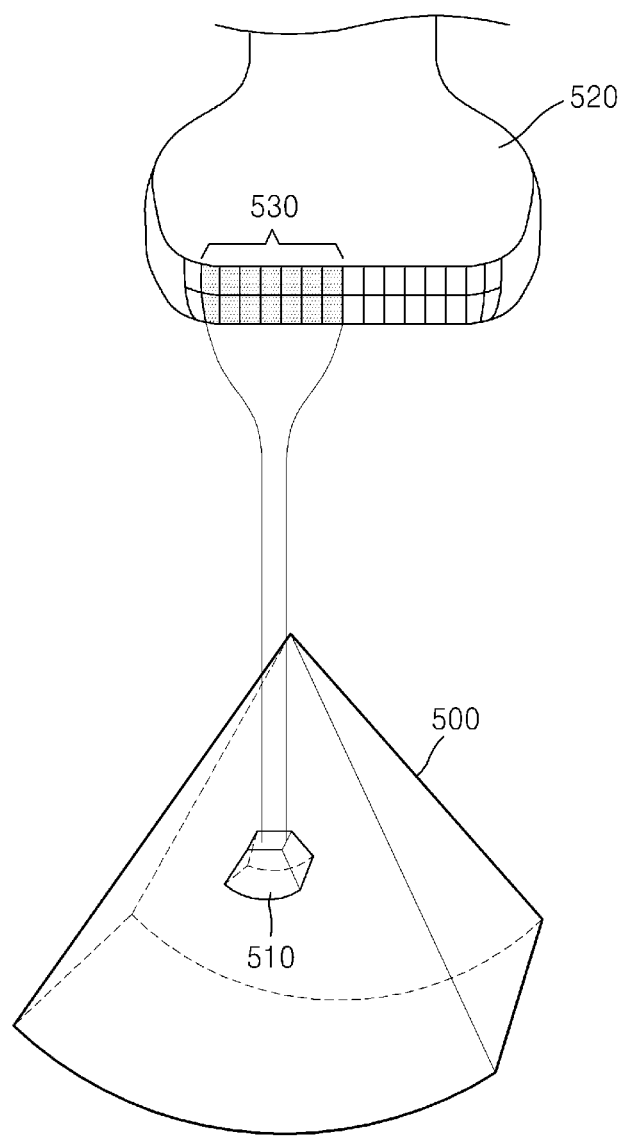
FIG. 6 is a diagram for describing determining of a cell corresponding to a sub volume by using a transducer, according to an embodiment of the present invention.

FIG. 6 is a diagram for describing determining of a cell corresponding to the sub volume 510 by using a transducer, according to an embodiment of the present invention. When the sub volume 510 in the 3D ultrasound image 500 is determined, the ultrasound diagnostic apparatus 100 determines at least one cell corresponding to the sub volume 510, from among a plurality of cells included in the transducer. In FIG. 6, the transducer including the plurality of cells is prepared in a probe 520.

Meanwhile, the ultrasound diagnostic apparatus 100 may determine at least one cell whose corresponding sub volume 510 is scanned by focusing and emitting an ultrasound signal via a steering process. A dark region 530 in FIG. 6 denotes the one or more cells whose corresponding sub volume 510 is scanned. In other words, the ultrasound diagnostic apparatus 100 may detect a cell whose corresponding sub volume 510 is scanned by analyzing the plurality of cells included in the transducer.

Meanwhile, in the probe 520 of FIG. 6, the transducer is in a linear array. However, alternatively, the transducer may be in a curvilinear array or a phased array. Alternatively, as described above with reference to FIG. 1, the probe 520 may be a matrix probe wherein cells of a transducer are arranged according to 2D coordinates.

Figure 7:
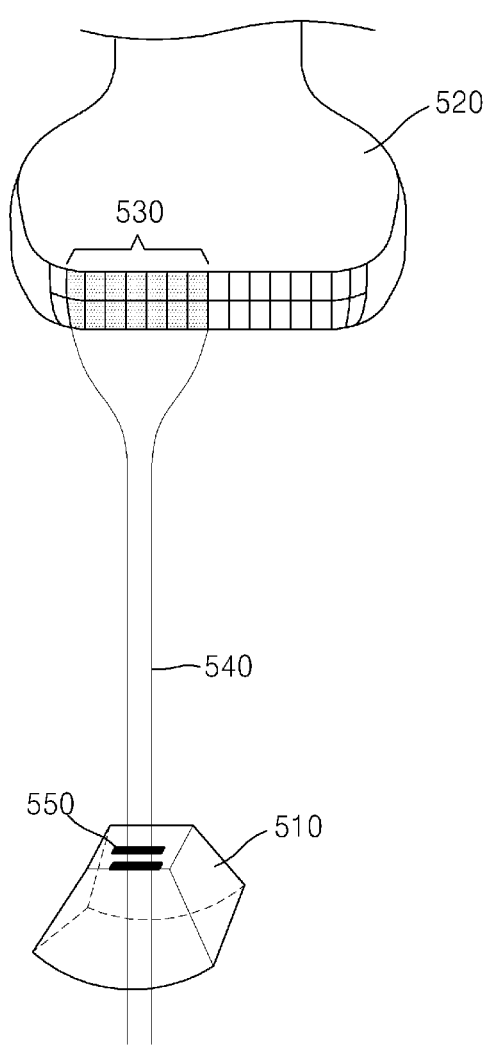
FIG. 7 is a diagram for describing locating of a sample volume on a scan line, according to an embodiment of the present invention.

FIG. 7 is a diagram for describing locating of a sample volume 550 on a scan line 540, according to an embodiment of the present invention. In FIG. 7, the scan line 540 irradiated by one or more cells located in the dark region 530 is displayed on a screen. The scan line 540 of FIG. 7 is thickly illustrated for convenience of description, and may be displayed having different thicknesses and shapes.

The ultrasound diagnostic apparatus 100 locates the sample volume 550 on the scan line 540. The sample volume 550 displayed in "=" on the screen is located at a depth of the target for measuring a Doppler signal, wherein a length (i.e., a range gate) of the sample volume 550 may be adjusted by a system or via a user input.

Meanwhile, while the ultrasound diagnostic apparatus 100 locates the sample volume 550 on the scan line 540, the sample volume 550 may be located according to a user input. In other words, the ultrasound diagnostic apparatus 100 may receive a user input for selecting any one location on the scan line 540, and locate the sample volume 550 at the location according to the received user input.

Then, the ultrasound diagnostic apparatus 100 may measure the Doppler signal with respect to the sample volume 550, thereby measuring a moving direction and a moving speed of the target in real time.

Figure 8:
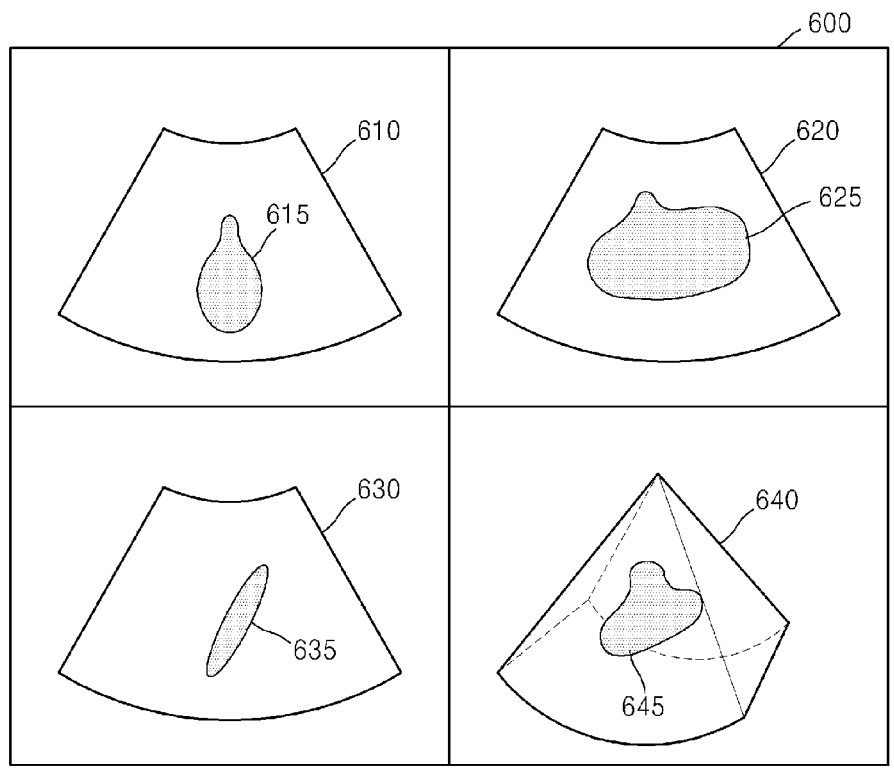
FIG. 8 is a diagram for describing displaying of volume data and sliced images, according to an embodiment of the present invention.

FIG. 8 is a diagram for describing displaying of volume data and sliced images 610, 620, and 630, according to an embodiment of the present invention. In FIG. 8, the ultrasound diagnostic apparatus 100 displays the three sliced images 610, 620, and 630, and a 3D ultrasound image 640 on a screen 600.

The sliced images 610, 620, and 630 displayed by the ultrasound diagnostic apparatus 100 are cross-sectional ultrasound images obtained by cutting the 3D ultrasound image 640. In other words, the ultrasound diagnostic apparatus 100 may cut the 3D ultrasound image 640 to obtain and display the sliced images 610, 620, and 630 crossing each other at right angles in a color region 645. In other words, the ultrasound diagnostic apparatus 100 may obtain and display the sliced images 610, 620, and 630 based on a color component of the 3D ultrasound image 640. The sliced images 610, 620, and 630 may respectively be sliced images of an A plane image, a B plane image, and a C plane image.

Also, since the sliced images 610, 620, and 630 are ultrasound images passing through the color region 645, the sliced images 610, 620, and 630 may respectively include color components 615, 625, and 635 that are parts of the color region 645.

The ultrasound diagnostic apparatus 100 may determine a sub volume based on the color components 615, 625, and 635 of the sliced images 610, 620, and 630. In other words, the ultrasound diagnostic apparatus 100 may determine a sub volume for locating a sample volume, at any one location of a region including the color components 615, 625, and 635. Then, the ultrasound diagnostic apparatus 100 may determine a cell whose corresponding sub volume is scanned, from a transducer.

Figure 9:
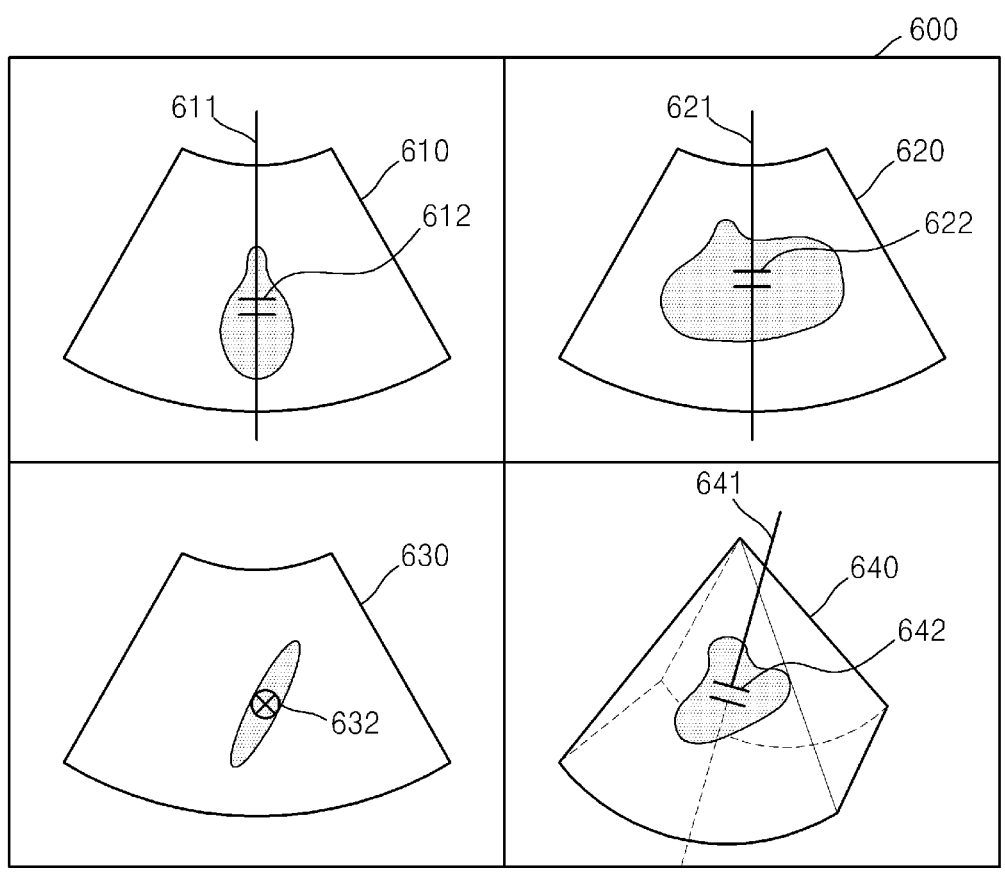
FIG. 9 is a diagram for describing displaying of a scan line and locating of sample volumes, according to an embodiment of the present invention.

FIG. 9 is a diagram for describing displaying of scan lines 611, 621, and 641 and locating of sample volumes 612, 622, 632, and 642, according to an embodiment of the present invention. Like FIG. 8, FIG. 9 illustrates the three sliced images 610, 620, and 630, and the 3D ultrasound image 640.

The ultrasound diagnostic apparatus 100 may display the scan lines 611, 621, and 641 for scanning the sub volume determined in FIG. 8 on an ultrasound image. In other words, the ultrasound diagnostic apparatus 100 may analyze a cell whose corresponding sub volume is scanned from among a plurality of cells included in a transducer, and may display the scan lines 611, 621, and 641 irradiated by one or more determined cells on the sliced images 610, 620, and 630, and the 3D ultrasound image 640. Meanwhile, the sliced image 630 displayed at the bottom left is marked "X" since a scan line is perpendicular to the sliced image 630. In other words, the ultrasound diagnostic apparatus 100 may display the scan lines 611, 621, and 641 irradiated by the cells according to a respective ultrasound image.

Then, the ultrasound diagnostic apparatus 100 locates the sample volumes 612, 622, 632, and 642 for measuring a Doppler signal on the scan lines 611, 621, and 641. In other words, the scan lines 611, 621, and 641, and the sample volumes 612, 622, 632, and 642 are respectively displayed on a plurality of ultrasound images displayed on the screen 600, when, in actuality, a sample volume is located on just one scan line scanning a sub volume. For example, the ultrasound diagnostic apparatus 100 may display the scan line 641 and the sample volume 642 displayed on the 3D ultrasound image 640 at the bottom right, on the sliced images 610, 620, and 630.

Then, the ultrasound diagnostic apparatus 100 may measure a Doppler signal with respect to the sample volumes 612, 622, 632, and 642 located on the scan lines 611, 621, and 641. In other words, the ultrasound diagnostic apparatus 100 may measure a Doppler signal at a desired depth by scanning a target in real time so as to diagnose the target.

The embodiments of the present invention may be written as computer programs and may be implemented in general-use digital computers that execute the programs using a computer readable recording medium. In addition, a data structure used in the embodiments of the present invention may be written in a computer readable recording medium through various means. Examples of the computer readable recording medium include magnetic storage media (e.g., ROM, floppy disks, hard disks, etc.), optical recording media (e.g., CD-ROMs, or DVDs), etc.

According to the ultrasound diagnostic method, the ultrasound diagnostic apparatus, and the computer readable recording medium, a user may accurately locate a sample volume for measuring a Doppler signal. In other words, reliability of the Doppler signal, which differs according to skills of the user, may be improved.

In addition, by locating the sample volume by using volume data, unlike locating a sample volume on a 2D ultrasound image, the user may accurately measure the Doppler signal at a desired location.

While this invention has been particularly shown and described with reference to embodiments thereof, it will be understood by those of ordinary skill in the art that various changes in form and details may be made therein without departing from the spirit and scope of the invention as defined by the appended claims. The embodiments should be considered in a descriptive sense only and not for purposes of limitation. Therefore, the scope of the invention is defined not by the detailed description of the invention but by the appended claims, and all differences within the scope will be construed as being included in the present invention.

What is claimed is:

1. An ultrasound diagnostic method comprising:
   obtaining a sub volume whose Doppler signal is to be measured based on a color component of at least one sliced image by cutting a 3-dimensional (3D) image according to 3-dimensional (3D) volume data of a target in a predetermined direction;
   determining a cell corresponding to the sub volume from among a plurality of cells included in a transducer;
   displaying the at least one sliced image;
   displaying a scan line on each of the at least one sliced image, wherein the scan line is irradiated by the determined cell;
   displaying direction information of the scan line on the at least one sliced image; and
   locating a sample volume for obtaining a Doppler signal on the scan line.

2. The ultrasound diagnostic method of claim 1, wherein the sub volume is determined based on a user input for selecting any one location on the at least one sliced image.

3. The ultrasound diagnostic method of claim 1, wherein the determining comprises determining at least one cell whose corresponding sub volume is scanned from among the plurality of cells.

4. The ultrasound diagnostic method of claim 1, wherein the locating comprises locating the sample volume based on a user input for selecting any one location on the scan line.

5. The ultrasound diagnostic method of claim 1, further comprising measuring the Doppler signal of the sample volume.

6. The ultrasound diagnostic method of claim 1, wherein the color component comprises information about a blood flow.

7. The ultrasound diagnostic method of claim 1, further comprising generating the 3D volume data by using a matrix probe including the plurality of cells arranged according to 2D coordinates.

8. The ultrasound diagnostic method of claim 1, further comprising generating the 3D volume data by combining at least one piece of volume data obtained according to a cardiac cycle of the target.

9. A non-transitory computer-readable recording medium having recorded thereon a program for executing the method of claim 1.

10. An ultrasound diagnostic apparatus comprising:
    a transducer configured to scan a target;
    an image processor configured to generate 3-dimensional (3D) volume data of the target, and to obtain at least one sliced image by cutting a 3D image according to the 3D volume data in a predetermined direction;
    a sub volume extractor configured to obtain a sub volume whose Doppler signal is to be measured, based on a color component of the at least one sliced image;
    a cell determiner configured to determine a cell corresponding to the sub volume from among a plurality of cells included in the transducer;
    a display unit configured to:
      display the at least one sliced image;
      display a scan line on each of the at least one sliced image, wherein the scan line is irradiated by the determined cell; and
      display direction information of the scan line on the at least one sliced image; and
    a Doppler processor configured to locate a sample volume for obtaining a Doppler signal, on the scan line.

11. The ultrasound diagnostic apparatus of claim 10, wherein the sub volume is determined based on a user input for selecting any one location on the at least one sliced image.

12. The ultrasound diagnostic apparatus of claim 10, wherein the cell determiner determines at least one cell whose corresponding sub volume is scanned from among the plurality of cells.

13. The ultrasound diagnostic apparatus of claim 11, further comprising a user interface configured to receive a user input for selecting any one location on the scan line, wherein the Doppler processor locates the sample volume based on the user input.

14. The ultrasound diagnostic apparatus of claim 10, wherein the Doppler processor measures the Doppler signal of the sample volume.

15. The ultrasound diagnostic apparatus of claim 10, wherein the color component comprises information about a blood flow.

16. The ultrasound diagnostic apparatus of claim 10, wherein the transducer comprises a matrix probe including the plurality of cells arranged according to 2D coordinates, and the image processor generates the 3D volume data based on data obtained by using the matrix probe.

17. The ultrasound diagnostic apparatus of claim 10, wherein the image processor generates the 3D volume data by combining at least one piece of volume data obtained according to a cardiac cycle of the target.

\* \* \* \* \*